United States Patent
Pitzurra

[11] Patent Number: 6,133,020
[45] Date of Patent: Oct. 17, 2000

[54] APPARATUS FOR DETERMINING THE NUMBER OF MICROORGANISMS IN THE AIR AND A METHOD OF OPERATING SAID APPARATUS

[76] Inventor: Ovidio Pitzurra, Alte Landstrasse 23, CH-9450 Altstätten, Switzerland

[21] Appl. No.: 08/981,797
[22] PCT Filed: May 7, 1997
[86] PCT No.: PCT/CH97/00176
  § 371 Date: Mar. 23, 1998
  § 102(e) Date: Mar. 23, 1998
[87] PCT Pub. No.: WO97/42304
  PCT Pub. Date: Nov. 13, 1997

[30] Foreign Application Priority Data

May 7, 1996 [CH] Switzerland .............................. 1163/96

[51] Int. Cl.[7] .............................. C12M 1/26; C12Q 1/24
[52] U.S. Cl. .......................... 435/287.1; 435/30; 435/34; 435/286.3; 435/287.3; 435/309.1
[58] Field of Search .................................. 435/3, 30, 31, 435/34, 39, 40, 287.1, 287.3, 287.9, 288.3, 309.1, 309.4, 286.3, 286.6; 73/864.71

[56] References Cited

U.S. PATENT DOCUMENTS 3,001,914  9/1961  Andersen .............................. 435/288.3
4,468,914  9/1984  Pestes .

FOREIGN PATENT DOCUMENTS

| 36 28 155 | 2/1988 | Germany . |
| 43 00 231 | 12/1993 | Germany . |
| 52-134081 | 11/1977 | Japan . |
| 62-272967 | 11/1987 | Japan .................................. 435/286.3 |
| 937515 | 6/1982 | U.S.S.R. .............................. 435/288.3 |
| 1546481 | 2/1990 | U.S.S.R. .............................. 435/287.1 |
| 1620476 | 1/1991 | U.S.S.R. .............................. 435/287.1 |
| 804586 | 11/1958 | United Kingdom ................ 435/288.3 |
| 92/12233 | 7/1992 | WIPO .................................. 435/286.3 |

*Primary Examiner*—William H. Beisner
*Attorney, Agent, or Firm*—Browdy and Neimark

[57] ABSTRACT

The invention concerns an apparatus which has holder stations (41, 42) for individual parts (3, 5) of a microorganism settlement device (1). This settlement device (1) comprises a lower part (30 with a nutrient medium (4) and a lid (5). The lower part (3) is located in the first holder station (41). The apparatus further has an actuating arrangement (10) designed such that the lid (5) can be moved in controlled manner between the two holder stations (41, 42).

16 Claims, 8 Drawing Sheets

FIG. 8

| Classes | | | | Room Evaluations | | |
|---|---|---|---|---|---|---|
| FS-209D Particles per m³ | CEE "KBE"* per m³ | IMA "KBE"* per cm² per hour | IMA "KBE"* per 60 cm² per hour** | Air Hygiene | Risk of Infection | "SED" Units |
| 10 | - | - | - | - | - | 0 |
| 100 | 5 | 0.00 – 0.06 | 0 – 4 | optimal | very low | 1 |
| 1000 | - | 0.07 – 0.30 | 5 – 18 | good | low | 2 |
| 10,000 | 100 | 0.40 – 0.60 | 19 – 36 | medium | medium | 3 |
| 100,000 | 500 | 0.70 – 0.90 | 37 – 54 | poor | high | 4 |
| 1,000,000 | - | >1.0 | >55 | very poor | very high | 5 |

APPARATUS FOR DETERMINING THE NUMBER OF MICROORGANISMS IN THE AIR AND A METHOD OF OPERATING SAID APPARATUS

BACKGROUND OF THE INVENTION

1. Technical Field of the Invention

The present invention relates to an apparatus for determining the number of microorganisms in air, with a device for the settlement of microorganisms, said device having a lower part and a cover, a nutrient or culture medium being located in the interior of the settlement device and to a method for operating this apparatus.

2. Prior Art

To detect the number of microorganisms, in particular germs, such as fungae, bacteria, etc., in air, it is known to cause germs suspended in the air to settle on a culture medium during a predetermined timespan. This culture medium is then covered and exposed to conditions which are conducive to the reproduction of the settled germs. After a predetermined timespan has elapsed, seats or zones on the culture medium which result from the growth of the settled germs are counted.

A so-called Petri dish, which has a lower part with a nutrient medium as well as a cover, is used for carrying out this method. The cover is removed from the lower part and the Petri dish is left open during a desired timespan. The Petri dish is then closed again by hand. The accuracy of this way of measuring the number of germs in air depends largely on the carefulness of the person who carries out these measurements manually. Moreover, this previously known method makes it necessary for the person carrying out such measurements to be present during the entire measuring operation. This is unfavorable, in particular, when such measurements have to be carried out outside the usual work time, in a place where access is difficult, etc.

OBJECT AND SUMMARY OF THE INVENTION

The object of the present invention is to eliminate said and further disadvantages of the prior art.

Embodiments of the present invention are explained in more detail below with reference to the accompanying drawings in which:

FIG. 8 shows a correlation table.

DETAILED DESCRIPTION OF THE PREFERRED EMBODIMENTS OF THE INVENTION

Figure 1:
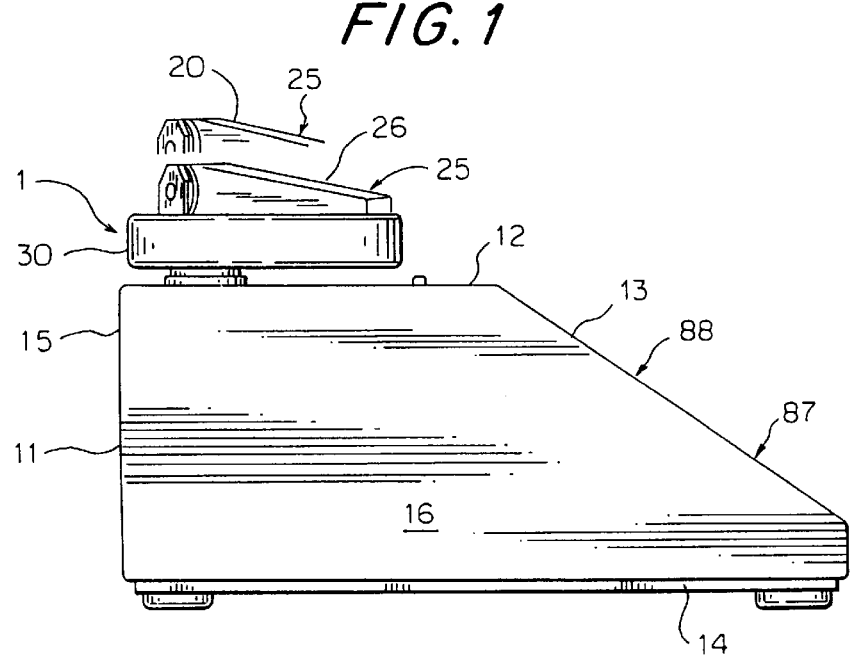
FIG. 1 shows a side view of a first version of the present apparatus.
Figure 2:
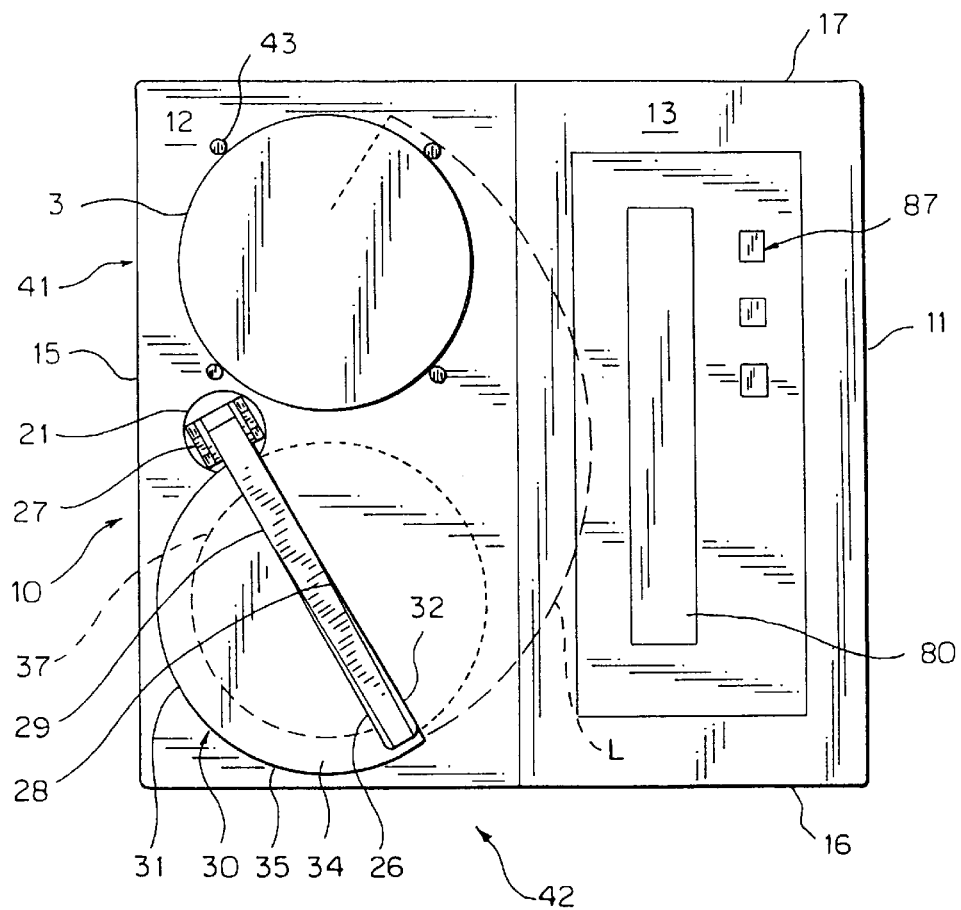
FIG. 2 shows a top view of the apparatus from FIG. 1.

FIG. 1 shows a side view of a first version of the present apparatus, whilst FIG. 2 shows a top view of the apparatus from FIG. 1. This apparatus serves for determining the number of germs in air, and it comprises a device 1 for the settlement of germs and an arrangement 10 for actuating this settlement device 1.

Figure 5:
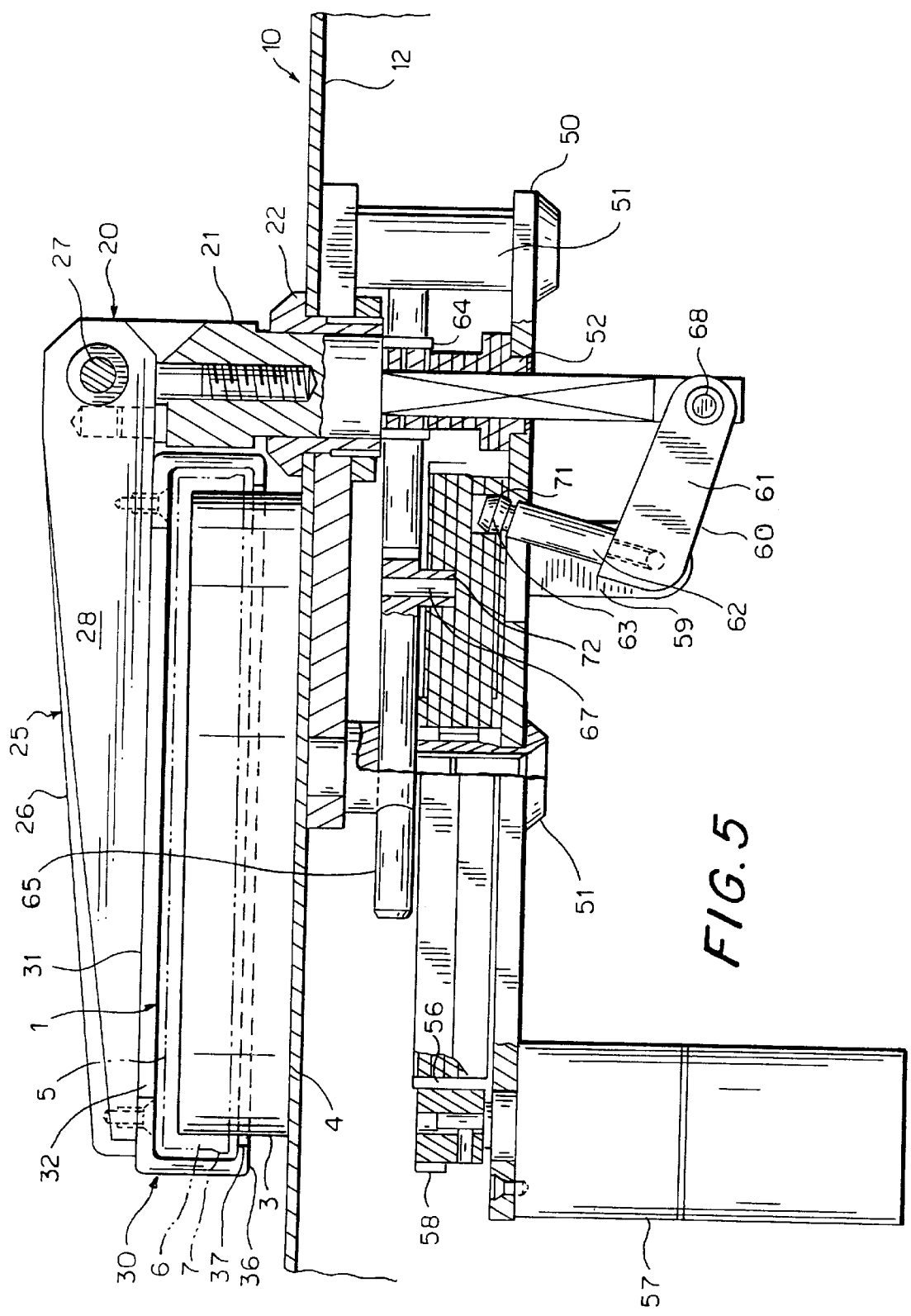
FIG. 5 shows the mechanical part of the present apparatus partially in a vertical section.
Figure 6:
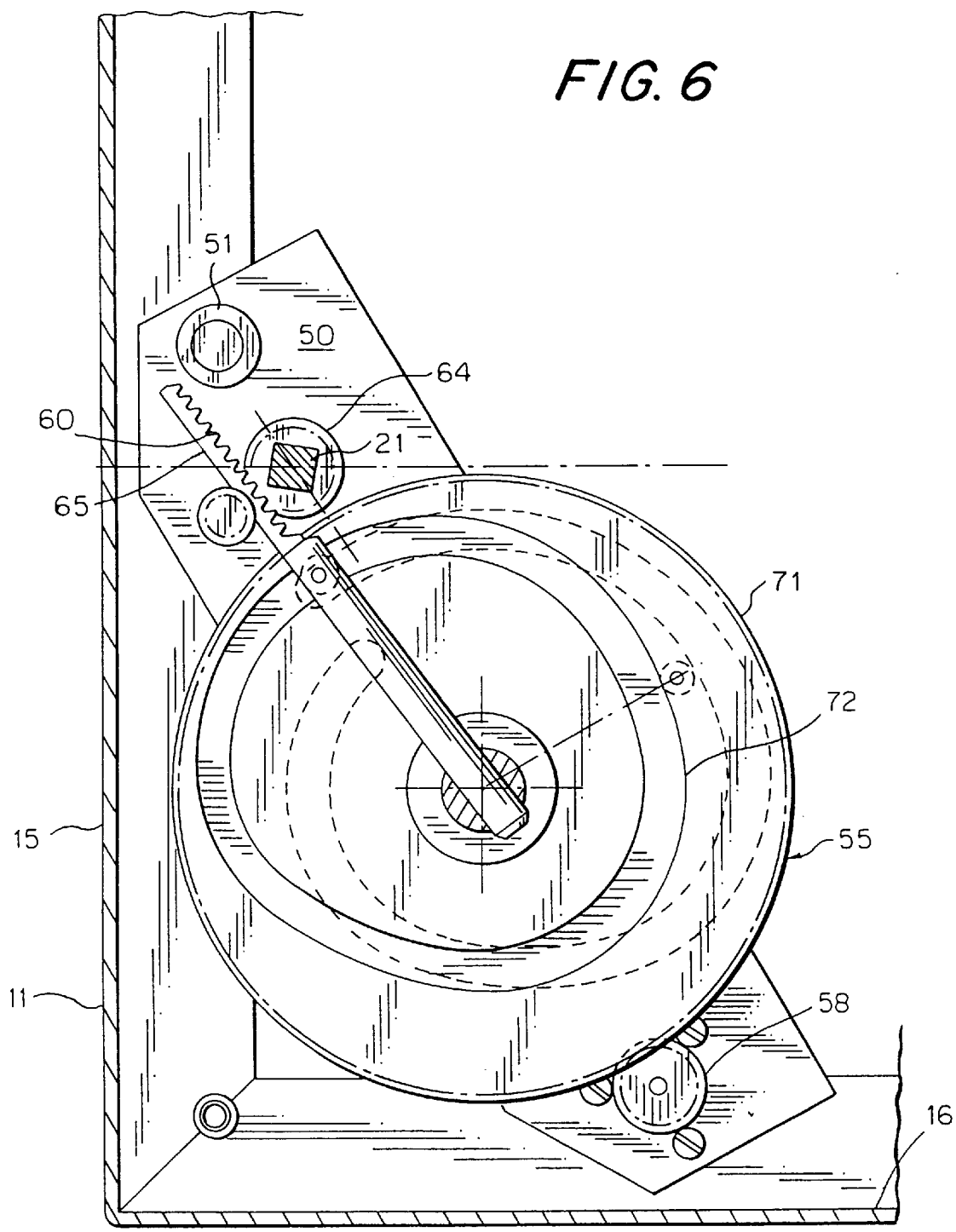
FIG. 6 shows a top view of the lower portion of the mechanical part from FIG. 5.
Figure 7:
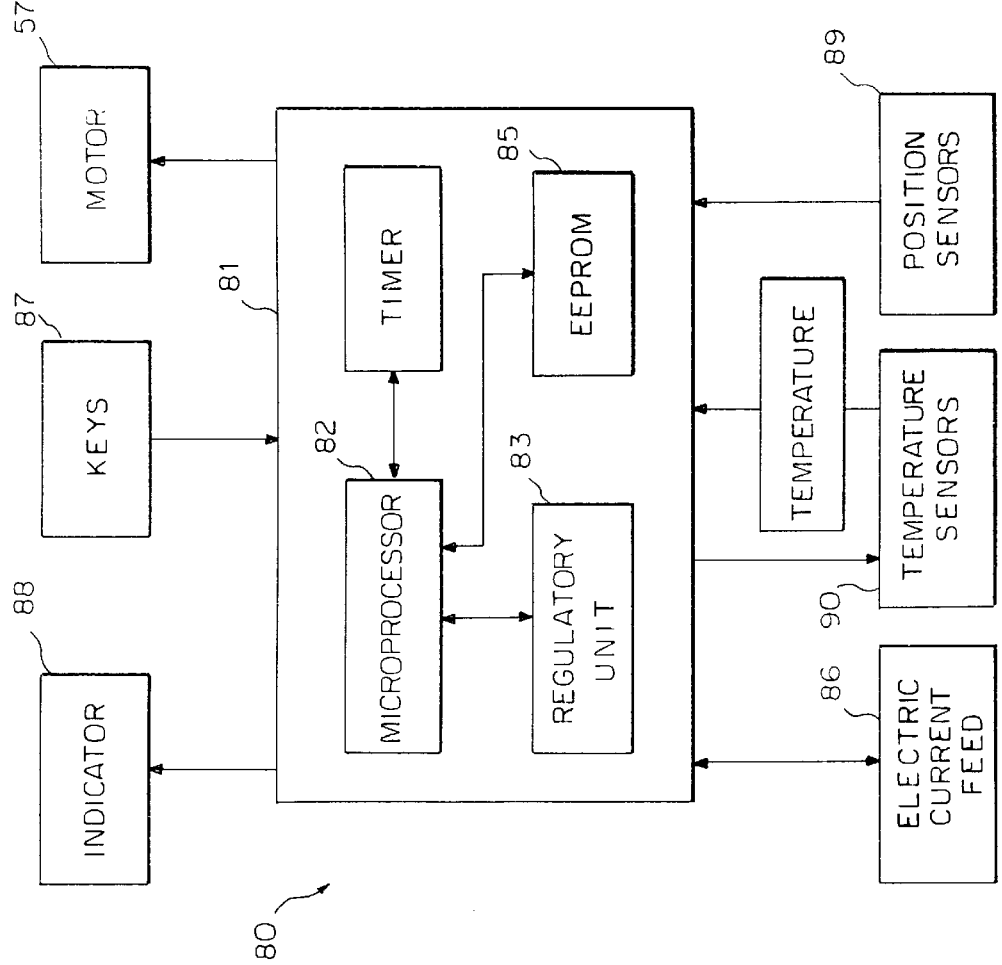
FIG. 7 shows a block diagram of the electrical part of the present apparatus.

The settlement device 1 is designed, in the present case, as a Petri dish known per se. The Petri dish 1 has a lower part 3 (FIG. 5) and a cover 5. The top side of the floor of the dish lower part 3 is covered with a culture or nutrient medium 4, on which microorganisms can settle when the Petri dish is open. The settled microorganisms can then reproduce on the nutrient medium 4 when the Petri dish 1 is closed. The culture medium 4 advantageously lies in a horizontal plane.

The settlement device 1 is designed, furthermore, in such a way that germs or particles can no longer pass into this device 1 during the incubation time. For this purpose, the cover 5 of the Petri dish 1 is designed in such a way that its edge part 6 hanging down also prevents germs from passing onto the lower part 3 during the incubation time. In this case, the cover 5 can rest on the upper edge of the dish lower part 3 either sealingly or so as to leave a gap between the cover 5 and the lower part 3. In order to form this gap, the underside of the dish cover 5 is provided with projections in a way known per se.

The actuating arrangement 10 comprises a housing 11 which has a horizontally extending upper wall 12, a display or indicator wall 13, a bottom 14, a rear wall 15 and side walls 16 and 17. The indicator wall 13 runs obliquely rearward from the housing bottom 14, so that the length or depth of the horizontally extending upper wall 12 is smaller than the length or depth of the bottom 14. Indicator elements and actuating means (not illustrated) of the present apparatus are mounted on the indicator wall 13.

The actuating arrangement 10 comprises, furthermore, a device 20 for handling the cover 5 of the settlement device 1. The handling device 20 is designed in such a way that the culture medium 4 can remain open during a desired timespan for the reception of microorganisms. This is achieved, inter alia, in that the cover 5 is moved by the handling device 20 in such a way that the cover 5 can be moved away from the lower part 3 and back to it again.

Figure 3:
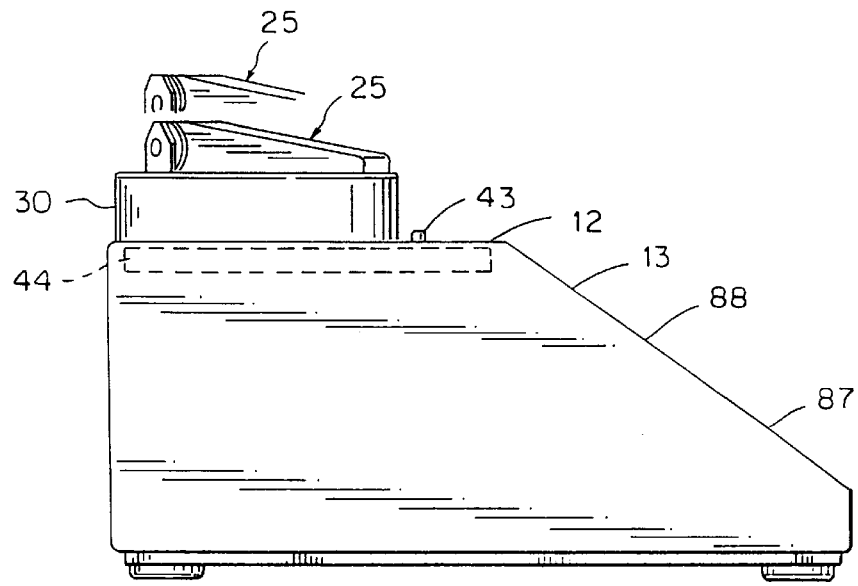
FIG. 3 shows a side view of a second version of the present apparatus.

The handling device 20 has a shaft 21 which runs virtually vertically and which passes through the upper wall 12 of the housing 11. In this case, this shaft 21 is mounted in a bearing 22 which is inserted in the upper wall 12 of the housing 11. This mounting is designed in such a way that the shaft 21 can not only rotate in the bearing 22, but also be displaced and down in its axial direction. Carrying means 25 for the cover 5 of the Petri dish 1 are articulated on the end part of the shaft 21, said end part being the upper or being located above the upper wall 12 of the housing 11. The displaceability of the shaft 21 in its axial direction is indicated in FIGS. 1 and 3 by two positions of the carrying means 25, said positions being located one above the other.

The carrying means 25 comprise an arm 26 which is articulated at one end on the upper end of the shaft 21 by means of a pin 27. The arm 26 is pivotable relative to the shaft 21 about this pin 27. The stops on the shaft 21, which limit the rotating movement of this arm 26, are designed in such a way that the arm 26 can rotate between its virtually horizontal and its virtually vertical position. The rotating arm 26 has a quadrangular cross-section, two of the sides 28 and 29 of the latter extending vertically. FIG. 2 illustrates the arm 26 in its retracted position. When the arm 26 is in this position, the lower part 3 of the Petri dish 1 is free and germs or the like can settle on the culture medium 4. The first of said side faces 28 of the arm 26 is the front side of the arm 26. A curved line L shows the path of a point located at the free end of the arm 26, while this apparatus is in operation.

A carrier 30 for the cover 5 of the Petri dish 1 is fastened to the underside of the free end part of the pivoting lever 26. This carrier 30 has a horizontally extending baseplate 31 which has a virtually semicircular contour (FIG. 2). The rectilinearly extending edge 32 of the baseplate 31 is engaged to the front side 28 of the pivoting arm 26, in such a way that this edge 32 runs parallel to the front side 28 of the arm 26. Consequently, the virtually semicircular portion 33 of the baseplate 31 projects from the rear side 29 of the pivoting arm 26. An essentially vertically extending and also semicircularly extending side wall 35 of this carrier 30 projects downward from the semicircular edge 34 of the baseplate 31. The lower edge of this side wall 35 has adjoining it a gripping wall 36 which has the shape of a portion of a flat and narrow ring. The outer edge of this gripping wall 36 adjoins the lower edge of said side wall 35. The inner edge 37 of this gripping wall 36 is free. The baseplate 31, side wall 35 and gripping wall 36 are expediently in one piece.

The radius of the inner edge 37 on the gripping ring 36 corresponds to the radius of the lower part 3 of the Petri dish 1. By contrast, the radius of the side wall 35 of the carrier 30 corresponds to the largest radius of the cover 5 of the Petri dish 1, that is to say to the radius of the lower edge 7 of the hanging-down side wall 6 of the cover 5. The height of the side wall 35 of the carrier 30 corresponds to the height of said side wall 6 of the cover 5. The expression "corresponds" means, here, that said dimensions of the carrier 30 are at least as large as the corresponding dimensions of the Petri dish 1. The dimensions on the carrier 30 may be somewhat larger than the corresponding dimensions of the Petri dish 1, so that the present apparatus can operate without any friction. In fact, the carrier 30 must be dimensioned in such a way that it can receive and transport the cover 5 without any difficulty. For this purpose, the depth, or dimension perpendicular to the arm 26, of the essentially semicircular baseplate 31 may be somewhat larger than the radius of the lower edge 7 on the cover 5 of the Petri dish 1. This additional depth of the baseplate 31 may correspond, for example, to the width of the arm 26, that is to say to the distance between the front wall 28 and the rear wall 29 of the arm 26. The radius of the inner edge 37 of the gripping wall and the width of this gripping wall 36 must be such that this wall 36 reliably engages under the lower edge 7 of the cover 5 of the Petri dish 1 and holds said edge reliably during the pivoting movement of the carrier 30.

The shaft 21 is arranged approximately in the middle of the length of the upper wall 12 of the apparatus housing 11. Reception stations 41 and 42 for the individual parts 3 and 5 of the Petri dish 1 are designed on the top side of the upper wall 12 on the left and right of the shaft 21. The lower part 3 of the Petri dish 1 is accommodated in the first reception station 41 and is held on the spot by means of position pins 43. This first reception station 41 comprises, furthermore, an electrothermal device 44 (FIGS. 3 and 4) which is advantageously located below the upper wall 12. By means of this electrothermal device 44, the lower part 3 of the Petri dish 1, together with the culture medium 4 and the germs settled on the latter, can, depending on the situation, either be heated (incubated), if the ambient temperature is low, or be cooled, if the ambient temperature is too high. This device 44 may contain a so-called Peltier element known per se.

Figure 4:
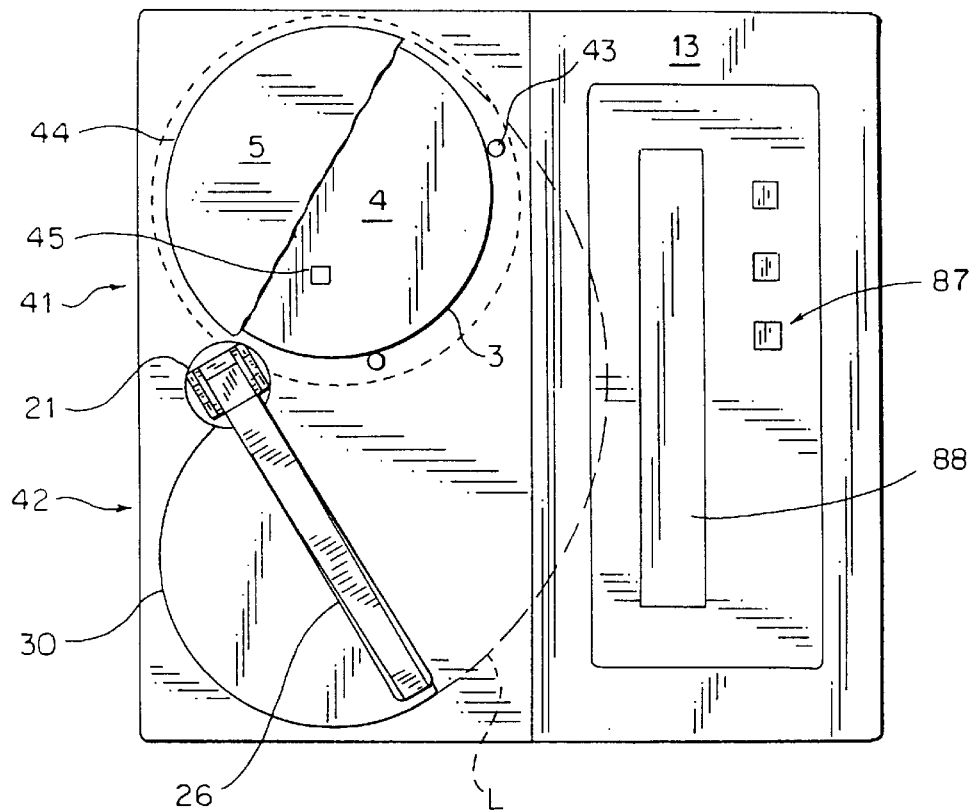
FIG. 4 shows a top view of the apparatus from FIG. 3.

FIG. 2 illustrates the carrier 30, together with the cover 5, in the second reception station 42, so that the cover 5 is in its position removed from the lower part 3. When the cover 5 is in this position, germs can settle on the culture medium 4 in the lower part 3. In FIG. 4, the cover 5 is illustrated placed on the lower part 3 in the region of the first reception station 41, so that further germs can no longer reach the culture medium 4. The carrier 30 is illustrated in its retracted position in the region of the second reception station 42, so that the cover 5 is free. FIG. 4 shows only a portion of the cover 5, so that it is possible to look into the interior of the Petri dish 1 having the culture medium 4. A colony 45 is indicated on that portion of the culture medium 4 which is shown in FIG. 4. This colony arose from a germ which reached the culture medium while the lower part 3 was uncovered.

Inside the housing 11 and below the upper wall 12 of the housing 11 is arranged an auxiliary plate 50 which is fastened to the underside of the upper wall 12 of the housing 11 by means of spacer pieces 51. This auxiliary plate 50 runs virtually parallel to the upper wall 12 and carries, inter alia, a second bearing 52 for the lower end part of the shaft 21. This second bearing 52 is aligned axially with the first bearing 22. The lower end part of the shaft 21 is designed to be so long that it projects out of the second or lower bearing 52.

A control disk 55, the circumferential part of which is provided with teeth 56, is mounted rotatably on the top side of the auxiliary plate 50. This circumferential part of the control disk 55 is assigned a drive motor 57, the pinion 58 of which meshes with the teeth 56 on the control disk 55.

At least one bearing block 59, on which a twoarmed angle lever 60 is mounted pivotably, projects from the underside of the auxiliary plate 50. The angle between the arms 61 and 62 of this angled lever 60 is about 90°. The free end of the first arm 61 of the angled lever 60 is articulated on the lower end of the shaft 21 by means of a pin 68. The second arm 62 of the angled lever 60 passes through a corresponding orifice in the auxiliary plate 50, so that the free end part of the second arm 62 of the angled lever 60 is located in the region of the control disk 55, specifically below the latter. The free end of the second arm 62 of the angled lever 60 is provided with a roller 63. The surface of this roller 63 has the shape of the surface of a spherical segment of two bases, in which the equator of the sphere is located in the middle of the height of this spherical segment.

In that region of the shaft 21 which is located between the two bearings 22 and 52, the shaft 21 is provided with a toothed rim 64 which surrounds the shaft 21 and which is firmly connected to the shaft 21. A horizontally arranged and displaceable rack 65 is provided, which is located above the control disk 55 and the teeth 66 of which mesh with the toothed rim 64 on the shaft 21. The underside of the rack 65 carries a guide roller 67 which projects virtually at right angles from the basic body of the rack 65.

A control cam 71 and 72 is designed in each case in the upper and the lower large-area side of the control disk 55. In the instance illustrated, these control cams 71 and 72 are designed as depressions or grooves in the large-area sides of the basic body of the control disk 55, said depressions or grooves having an essentially quadrangular cross section. The lower control cam 71 serves for controlling the vertical movement of the carrying means 25 for the cover 5 of the Petri dish 1. The roller 63 of the second arm 62 of the angled lever 60 is located in this control cam 71. The upper control cam 72 serves for controlling the pivoting movements of the carrier 30 of the carrying means 25 in the horizontal direction. The guide roller 67 on the rack 65 is located in this control cam 72.

The first control cam 71 has essentially the shape of a spiral with a single turn. When the control disk 55 executes a revolution, the roller 63 on the second arm 62 of the angled lever 60, said roller being located in this control cam 71, is displaced in the radial direction of the control disk 55. In this case, that end of the first arm 61 of this angled lever 60 which is connected to the shaft 21 moves the shaft 21 in the vertical direction. The shaft 21 moves either upward or downward, depending on the direction of rotation of the control disk 55. The second control cam 72 is nonround and has portions which allow a to and fro horizontal movement of the carrier 30 of the cover 5 or a standstill of this carrier 30. During these standstill portions, the carrier 30 is moved in the vertical direction by means of the first control cam 71, as described above.

The measures described make it possible for the carrying means 25 to execute simultaneously two movements which are necessary in order to move the cover 5 of the Petri dish between the first station 41 and the second station 42. Said measures also make it possible to place the cover 5 in the first station 41 onto the lower part 3 of the Petri dish 1. The carrier 30, without the cover 5, is then moved back again along the curve L into the second station 42 until it assumes the position which is illustrated in FIG. 2.

A Petri dish 1, in which its cover 5 is placed on its lower part 3, is brought into the first station 41 of the present apparatus by hand. After one of the operations has been selected, the carrier 30 for the cover 5 of the Petri dish 1 moves along the curve L out of the second station 42 into the first station 41, this carrier 30 being located in its lower position. This horizontal movement ends when the front edge 37 of the gripping wall 36 on the carrier 30 comes into the vicinity of the lower part 3 of the Petri dish 1 or even touches the side wall of this lower part 3. In this case, the gripping wall 36 of the carrier 30 comes to rest under the lower edge 7 of the side wall 6 of the cover 5. The shaft 21 is then moved upward, so that the cover 5 is lifted off from the lower part 3 due to the gripping wall 36 of the carrier 30 being located under the cover wall 6. The carrier 25, together with the cover 5, then moves back into the second station 42, said carrier being located in its upper vertical position.

After a timespan provided for the settling of germs on the culture medium 4 has elapsed, the carrier 25, together with the cover 5, moves toward the first station 41, said carrier still being in its upper position. In the first station 41, the carrier 30 is lowered, with the result that the cover 5 is set down on the lower part 3 of the Petri dish 1. In this lower position, the carrier 25 then moves back into the second station 42.

After the Petri dish 1 has been closed, germs which have settled on the culture medium 4 during the opening time of the Petri dish 1 can grow to form colonies 45. After a predetermined timespan, the number of said colonies is counted, and the number of microorganisms in the air can be inferred from this.

So that these and further work steps can be executed automatically, the apparatus is equipped with a control device 80. This control device 80 is accommodated in the housing 11 of the apparatus and contains a control unit 81 which comprises a microprocessor 82, a regulating unit 83, a timer 84 and an EEPROM 85. This control unit 81 is supplied by means of a feed 86 with electrical current which is also used for feeding the motor 57. The respective operating mode of the apparatus is entered by means of keys 87 which are located, together with indicator means 88 known per se, in the region of the indicator wall 13 of the apparatus housing 11. For the automatic control sequence, it is necessary to provide position sensors 89 for detecting the position of the carrier 30. These are arranged at respective points along the path L of the carrier 30. Furthermore, the control device 80 also comprises temperature sensors 90 which are mounted in the region of the first station 41.

The EEPROM 85 stores, inter alia, programs for handling the Petri dish 1. These programs may contain various conditions, such as, for example, time, temperature, etc., for the incubation of the settled microorganisms on the culture medium 4. Together with the selection of suitable culture media 4, such programs may be used for a selective capture of microorganisms.

Since the quantity of microorganisms in the air also depends on the height above the ground, it is expedient to provide a stand (not illustrated), on which the housing 11 of the apparatus is fastened. So that the density of the germs can be measured at different heights, the stand is designed in such a way that its height is adjustable.

FIG. 8 shows a table which indicates, inter alia, how the hygienic situation in rooms has been evaluated hitherto. The particulars in the first column of the table, although being relatively clear, use large numbers, which is cumbersome in practice. The evaluation (CEE) in the second column of the table in FIG. 8 does not cover all classes of air hygiene. The "IMA" columns work with particulars relating to ranges, which is likewise cumbersome. The evaluation interpreted in words in the two penultimate columns is inaccurate.

In the present case, the individual classes of room evaluation are assigned numbers from 1 to 5 which are directly related to the quantities of particles per $cm^2$ and per hour which are specified in the third column of the table from FIG. 8.

Figure 9:
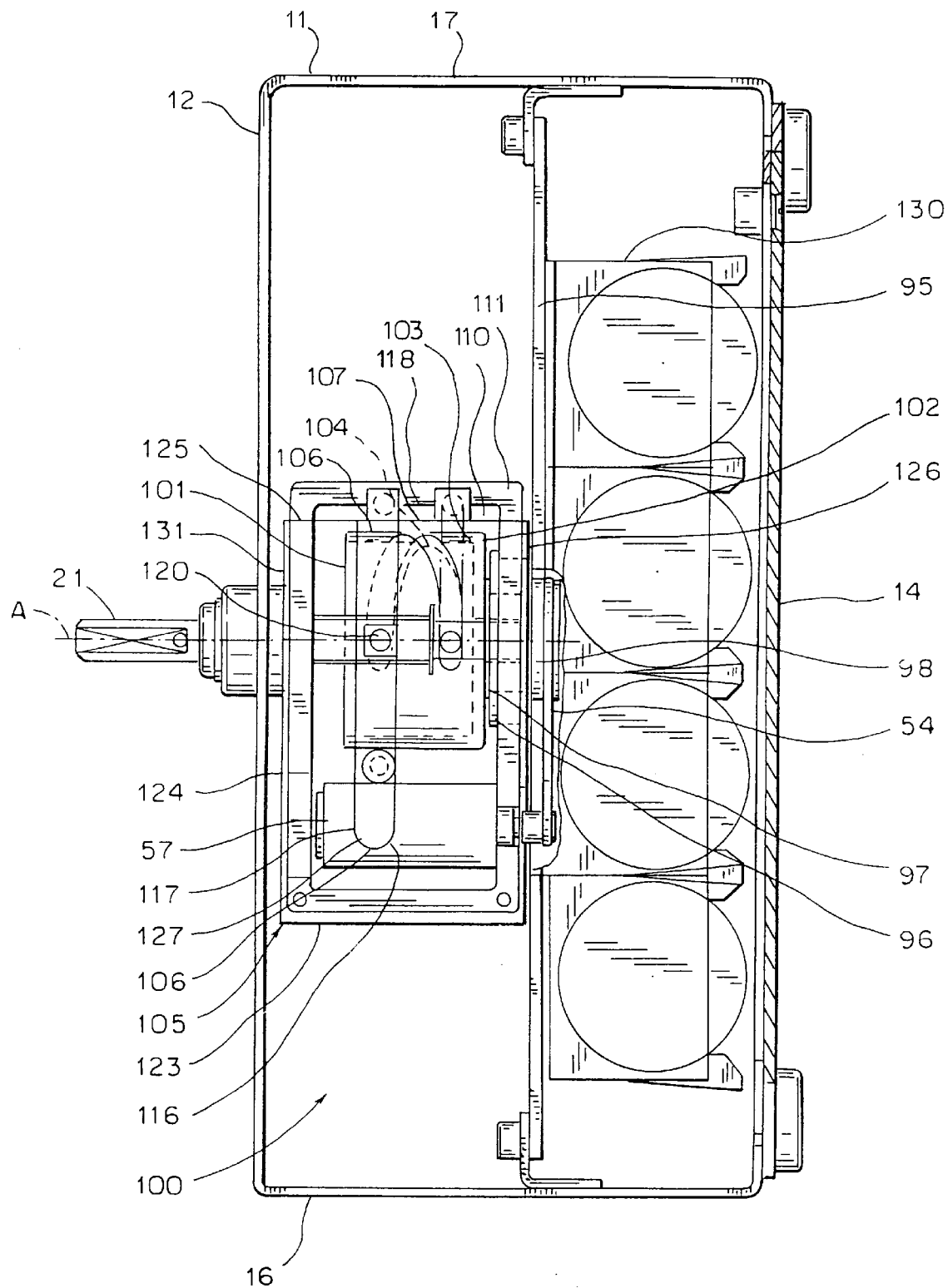
FIGS. 9 to 14 show a second actuating arrangement.
Figure 10:
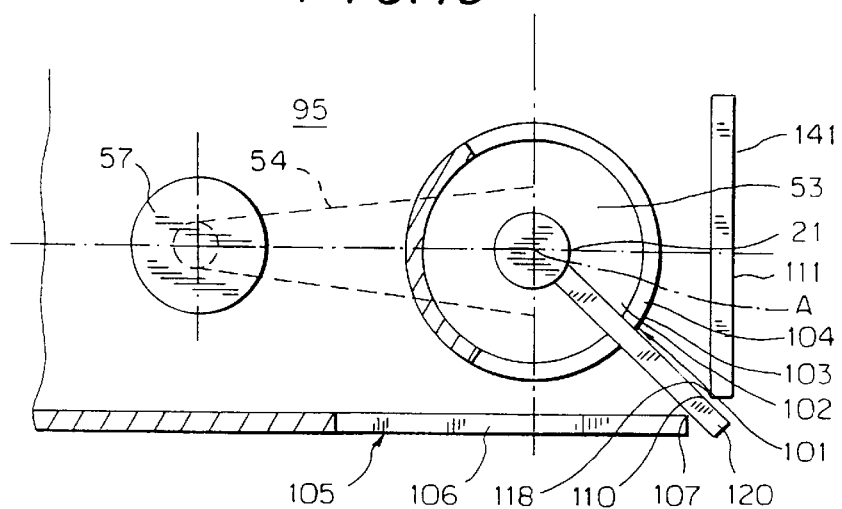
Figure 11:
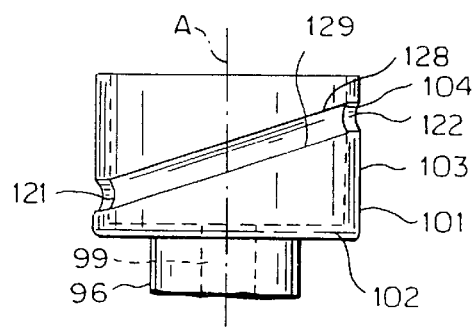
Figure 13:
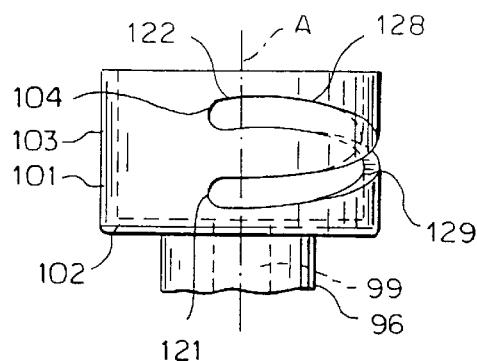
Figure 12:
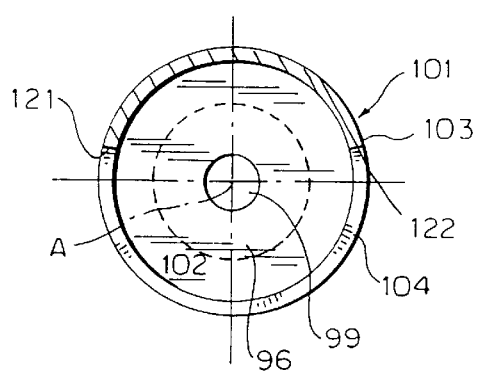
Figure 14:
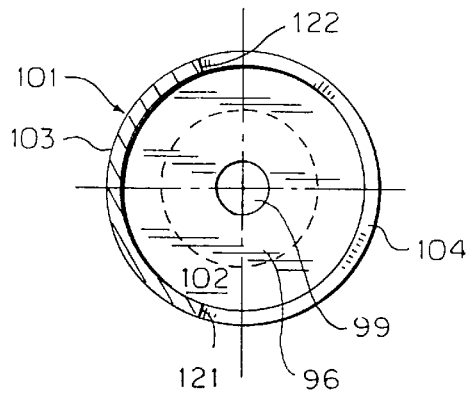

FIG. 9 shows a further possibility for the design of the present apparatus, specifically in a front view after the front wall of this apparatus has been removed. Arranged in the housing 11 of the apparatus is a carrying plate 95, on which a second possible version of the arrangement 100 for actuating the settlement device 1 is mounted. FIG. 10 shows a top view of the most important components of this arrangement 100.

The arrangement 100 comprises a crank 101 which is mounted rotatably or pivotably on the carrying plate 95. In the case illustrated, this crank 101 is essentially bowl-shaped or sleeve-shaped and has a bottom 102 (FIGS. 11 to 14), from which a cylindrical side wall 103 extends upward. The axis of rotation of this crank 101 runs vertically in the case illustrated and coincides with the main axis A of this arrangement 100.

The underside of the crank bottom 101 has adjoining it a hollow shaft 96 which is arranged in the middle of the crank bottom 102 and which carries the crank 101. This carrying shaft 96 is mounted rotatably or pivotably in a bearing 97. The pivoting shaft 21 passes through the orifice 99 in the carrying shaft 96 us [sic] is mounted both pivotably and longitudinally displaceably in this orifice 99. The axis of the carrying shaft 96 likewise coincides with the main axis A of this arrangement 100. The bearing 97 is embedded in the carrying plate 95, so that part of the carrying shaft 96 can project from the underside of the bearing 97. This portion of the carrying shaft 96 is provided with a disk 98 which is firmly connected to the crank 101 via the carrying shaft 96. This disk 98 is connected to the drive motor 57 of this arrangement 100 via a belt 54.

A slot 104 is made in the wall 103 of the crank 101, said slot constituting a perforation in the crank wall 103. This slot 104 runs obliquely with respect to the axis A. This means that one end 121 of the slot 104 is lower or nearer to the crank bottom 102 than the other end 122 of this slot 104. The angular length of the slot 104 is more than 180° and is advantageously 210°. The crank slot 104 has an upper longitudinal edge 128 and a lower longitudinal edge 129 which extend between the ends 121 and 122 of the slot 104 and run continuously.

The arrangement 100 comprises, furthermore, a guide plate 105 which is arranged next to the crank 101 and which runs virtually parallel to a plane, in which the main axis A of this arrangement 100 lies. The guide plate 105 is at a distance from the outside of the crank 101. In the instance illustrated, the basic body 131 of the plate 105 is essentially rectangular, the longer sides 124 and 126 of this rectangle 131 running horizontally. The shorter sides 123 and 125 of the rectangle 131 run vertically.

The guide plate 105 has a rectilinear long hole 106 which runs virtually horizontally, that is to say parallel to the longer sides 124 and 126 of the guide plate 105, and which is virtually at the same height as the upper end part 122 of the slot 104 in the crank 101. The long hole 106 is arranged in relation to the pivoting shaft 21 in such a way that the pivoting shaft 21 is located approximately in the middle of the length of the long hole. One of the ends of this long hole 106 is located in one of the sides 125 of the basic body 131 of the guide plate 105, so that the long hole 106 opens here and adjoins this side 125 of the guide plate 106. By contrast, the other end 127 of the long hole 106 is closed by means of a bottom. The long hole 106 comprises, furthermore, a lower edge 116 and an upper edge 117 which run likewise horizontally, that is to say parallel to the longitudinal sides 124 and 126 of the guide plate 105.

The plate 105 has, furthermore, a guide edge 107. This edge 107 constitutes a portion of that side 125 of the plate 105 in which the open end of the long hole 106 is located, the guide edge 107 extending between this open end of the long hole 106 and the underside 126 of the guide plate 105. This guide edge 107 thus runs virtually parallel to the main axis A of this arrangement 100.

The arrangement 100 also comprises a stop 111 which, in the instance illustrated, has an essentially plate-shaped basic body 141. This plate-shaped basic body 141 runs parallel to a plane, in which the main axis A of the arrangement 100 lies, said basic body being approximately at right-angles to the guide plate 105. That edge 118 of the stop plate 111 which is located nearest to the guide plate 105 is assigned to the guide edge 107 of the guide plate 105, specifically in such a way that a gap is free between these edges 107 and 118. The stop edge 118, although running parallel to the guide edge 107, is longer than the guide edge 107. The upper end of the stop edge 118 is higher than the upper end of the guide edge 107, so that a portion of the stop edge 118 is opposite the open mouth of the long hole 106 in the guide plate 105.

A bolt 120 is fastened at one end to the shaft 21 and projects virtually at right-angles from this shaft 21. The bolt 120 is arranged on the shaft 21 in such a way and designed to be so long that it can pass through the slot 104 in the crank 101 and that its free end part is located in the region of the guide plate 105. The cross section of the bolt 120 is circular. The width of the slot 104, of the long hole 106 and of the already mentioned gap between the guide edge 107 and the stop edge 118 corresponds to the diameter of the bolt 120, specifically in such a way that the bolt 120 can move in the slot 104, in the long hole 120 [sic] and in said gap with as little friction as possible.

In describing the mode of operation of this arrangement 100, we can start from the situation in which the bolt 120 is located at the bottom in the crank slot 104 and in the gap between the edges 107 and 118. In this case, the cover of the Petri dish is placed on the lower part of the latter. When the crank 101 is rotated clockwise by means of the drive 57, the bolt 120 butts on the guide edge 107 and, due to the ascent of the crank slot 104, the bolt 120 moves upward along this guide edge 107, until it has reached the height of the open mouth of the long hole 106 in the guide plate 105. During this phase, the pivoting shaft 21 coupled to the bolt 120 executes a lifting movement directed upward, and at the same time the cover of the Petri dish is lifted off from the lower part of the latter.

At the end of the lifting movement, the bolt 120 is opposite the open end of the long hole 106 in the guide plate 105. However, since the drive 57 drives the crank 101 further in the same direction, the bottom of the upper end 122 of the crank slot 104 presses the bolt 120 into the guide long hole 106 and moves said bolt in the long hole 106 until the bolt 120 butts on the long hole bottom 127. During this phase, the shaft 21 has executed a pivoting movement and, at the same time, the cover of the Petri dish has been removed from the lower part.

When the direction of rotation of the drive 57 is then reversed, the crank 101 moves counterclockwise. The bolt 120 is pressed against the open end of the long hole 106 by the upper and obliquely descending edge 128 of the crank slot 104 in this long hole 106. The bolt 120 moves in the long hole 106, until it butts on the stop edge 118 located opposite this end of the long hole. The shaft 21 has been pivoted back during this movement of the bolt 120, so that the cover of the Petri dish has been returned to the lower part of the latter.

The crank 101 is pivoted or rotated further in the same direction by the drive 57. In this case, the bolt 120 is in abutment on the stop edge 118, so that it cannot move any further in the horizontal direction. However, said gap between the edges 107 and 118 is now located under the bolt 120, and the bolt 120 is pressed into this gap by the descending slot 104. At the same time, the shaft 21 executes a lifting movement directed downward and the cover of the Petri dish is placed onto the lower part of the latter.

What is claimed is:

1. Apparatus for determining the number of microorganisms in air, with a settlement device (1) for the settlement of microorganisms, which has a lower part (3) and a cover (5), a nutrient medium (4) being located in an interior of the settlement device (1), with an arrangement (10) for actuating the cover (5) of the settlement device (1), with two reception stations (41, 42) for the settlement device (1), whereby the actuating arrangement (10) is designed in such a way that the cover (5) can be moved in a controlled way between the two reception stations (41, 42), and whereby the actuating arrangement (10) comprises a device (20) for handling the cover (5) and a device (80) for controlling the movements of the cover (5), wherein the handling device (20) comprises a shaft (21) which runs virtually vertically and which is arranged between the two reception stations (41, 42), wherein carrying means (25) for the cover (5) are engaged to a first end of the shaft (21), and means for the mechanical movement of the shaft (21) are engaged to a second end of the shaft (21), wherein the movement means comprise a motor (57) capable of being controlled by the control device (80), the movement means having, a control disk (55) which is driven by the motor (57), the control disk (55) having control cams (71, 72) and the movement means having a lever (60) and a rack (65) which are engaged to the control cams (71, 72) on the control disk (55) and to the shaft (21).

2. Apparatus according to claim 1, wherein the shaft (21) is vertically oriented and is surrounded with a toothed rim (64) in a region of its surface, that the rack (65) is horizontally arranged and displaceable and is equipped with teeth (66) which are form-locked with the toothed rim (64) of the rack (65).

3. Apparatus according to claim 2, wherein the control cams (71, 72) are grooves in the large-area sides of the control disk (55), that each side of the control (55) carries preferably one control cam and that a first cam (72) is engaged to the rack (65) and that a second cam (71) is assigned control of the horizontal movement of the carrying means (25) and is assigned control of the vertical movement of the carrying means (25) and is engaged to the lever (60).

4. Apparatus according to claim 3, wherein each the lever (60) and the rack (65) are equipped with roller (63, 65), said rollers (63, 65) being located in the grooves of the control cams (71, 72).

5. Apparatus according to claim 4, wherein the lever (60) is a two-armed lever comprising two arms (61 and 62) and that the angle between the arms (61, 62) of this lever (60) is about 90° and wherein the free end of a first arm (61) is articulated on the shaft (21) and wherein the free end of a second arm (62) is provided with the roller (63) for contacting the control cam.

6. Apparatus according to claim 4, wherein said roller has a spherical shape.

7. Apparatus according to claim 1, wherein the carrying means (25) comprise an arm (26) which is connected at a first end to the first end of the shaft (21), and in that a carrier (30) for the cover (5) of the dish (1) is mounted on a second end of the arm (26).

8. Apparatus according to claim 1, wherein the control device (80) comprises a microprocessor (82), a regulating unit (83), a timer (84) and an EEPROM (85) which are electrically connected together as well as means for manual actuation of the control device (80), in that sensors (89, 90) are connected to inputs of the control device (80), and in that the motor (57) is connected to one of the outputs of the control device (80).

9. Apparatus according to claim 1, wherein a thermoelectric device (44) is arranged in a region of a first reception station (41) of the two reception stations (41, 42), and in the thermoelectric device (44) may be a Peltier device.

10. Apparatus according to claim 1, wherein a stand is provided, on which remaining parts of the apparatus are mounted, and in that the stand may be designed in such a way that a height of the stand is adjustable.

11. Apparatus according to claim 1, wherein the settlement device (1) is a Petri dish.

12. Method for operating apparatus for determining the number of microorganisms in air, said apparatus having a settlement device (1) for the settlement of microorganisms, which has a lower part (3) and a cover (5), a nutrient medium (4) being located in an interior of the settlement device (1), with an arrangement (10) for actuating the cover (5) of the settlement device (1), with two reception stations (41, 42) for the settlement device (1), whereby the actuating arrangement (10) is designed in such a way that the cover (5) can be moved in a controlled way between the two reception stations (41, 42), and whereby the actuating arrangement (10) comprises a device (20) for handling the cover (5) and a device (80) for controlling the movements of the cover (5), wherein the handling device (20) comprises a shaft (21) which runs virtually vertically and which is arranged between the two reception stations (41, 42), wherein carrying means (25) for the cover (5) are engaged to a first end of the shaft (21), and means for the mechanical movement of the shaft (21) are engaged to a second end of the shaft (21), wherein the nutrient medium (4) is exposed to air during a predetermined timespan, in such a way that microorganisms present in the air can settle on the nutrient medium (4), in that the nutrient medium is covered after a predetermined timespan has elapsed, in that after an incubation time has elapsed, visible colonies caused by the microorganisms on the nutrient medium are counted, and a value for an air germ count is obtained from the visible colonies, and in that the evaluation of a room investigated is express on a basis of the air germ count by particles per $cm^2$ per hour.

13. Apparatus for determining the number of microorganisms in air, with settlement device (1) for the settlement of microorganisms, which has a lower part (3) and a cover (5), a nutrient medium (4) being located in an interior of the settlement device (1), with an arrangement (100) for actuating the cover (5) of the settlement device (1), whereby the actuating arrangement (100) is designed in such a way that the cover (5) can be moved in a controlled way between the two reception stations (41, 42), and whereby the actuating arrangement (100) comprise a device (20) for handling the cover (5) and a device (80) for controlling movements of the cover (5), wherein the handling device (20) comprises a shaft (21) which runs virtually vertically and which is arranged between the two reception stations (41, 42), wherein carrying means (25) for the cover (5) are engaged to a first end of the shaft (21), and means for the mechanical movement of the shaft (21) are engaged to a second end of the shaft (21), wherein the movement means comprise a motor (57) capable of being controlled by the control device (80), the movement means having a control crank (101) which is driven by the motor (57), the crank (101) having a control slot (104) and the movement means having a bolt (120) which is engaged to the slot (104) and to the shaft (21).

14. Apparatus according to claim 13, wherein the crank (101) is essentially sleeve-shaped, having an inner orifice (99) and a cylindrical side wall (103), and wherein the crank (101) has an axis of rotation that runs essentially vertically and coincides with the longitudinal axis A of the arrangement (100) and the shaft (21), said shaft (21) being mounted both pivotably and longitudinally displaceable in the orifice (99) of the crank (101).

15. Apparatus according to claim 14, wherein the control slot (104) is executed as a perforation in the cylindrical side wall (103) of the crank and is running obliquely with respect to the longitudinal axis A of the arrangement (100), wherein the angular length of the slot (104) is more than 180°, and wherein the bolt (120) is fastened at one end to the shaft (21) and projects from the shaft (21) in such a way that it can pass through the slot (104) in the crank (101) and is with its free end movably beared on a guide plate or means (105).

16. Apparatus according to claim 15, wherein the angular length is more than 210°.

\* \* \* \* \*